United States Patent [19]
Zwirkoski

[11] Patent Number: 4,796,633
[45] Date of Patent: Jan. 10, 1989

[54] METHOD AND APPARATUS FOR IN VITRO CALIBRATION OF OXYGEN SATURATION MONITOR

[75] Inventor: Lori J. Zwirkoski, Tustin, Calif.

[73] Assignee: American Hospital Supply Corporation, Evanston, Ill.

[21] Appl. No.: 748,485

[22] Filed: Jun. 25, 1985

[51] Int. Cl.⁴ .............................. A61B 5/00; G01J 1/02
[52] U.S. Cl. ....................................... 128/634; 73/1 G; 250/252.1; 356/243
[58] Field of Search ............... 128/633, 634, 665, 666; 73/1 G; 250/252.1; 356/39–42, 243

[56] References Cited

U.S. PATENT DOCUMENTS 3,807,390 4/1974 Ostrowski et al. .
3,977,995 8/1976 Louderback et al. ............ 356/42 X
4,050,450 9/1977 Polanyi et al. .
4,235,245 11/1980 Naito .................................... 128/756
4,322,164 3/1982 Shaw .
4,353,868 10/1982 Joslin et al. ...................... 128/759 X Primary Examiner—Kyle L. Howell
Assistant Examiner—John C. Hanley
Attorney, Agent, or Firm—Gordon L. Peterson

[57] ABSTRACT

A calibration reference apparatus comprising an elongated peripheral tubular wall open at one end and an end wall closing the other end of the tubular wall. The tubular wall and the end wall are integrally molded. The end wall defines a curved cavity opening toward the open end of the tubular wall. The calibration reference apparatus is adapted to receive a light guide through the tubular wall and in the cavity. A stop limits the extend to which the light guide can be advanced into the cavity whereby an end face of the light guide is spaced from a region of the surface to define a gap. The end wall and the gap are adapted to return a known ratio of the light directed into the gap from the end face of the light guide.

15 Claims, 2 Drawing Sheets

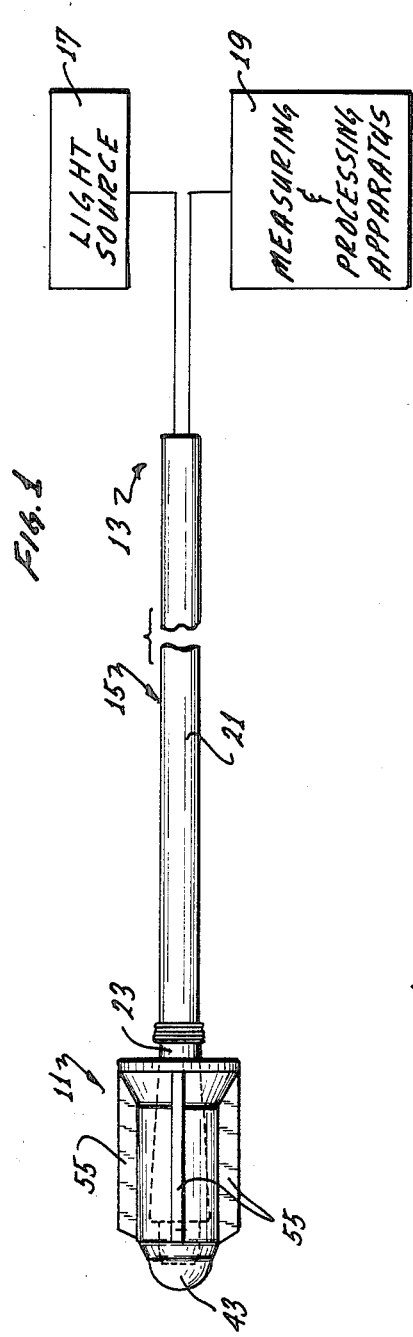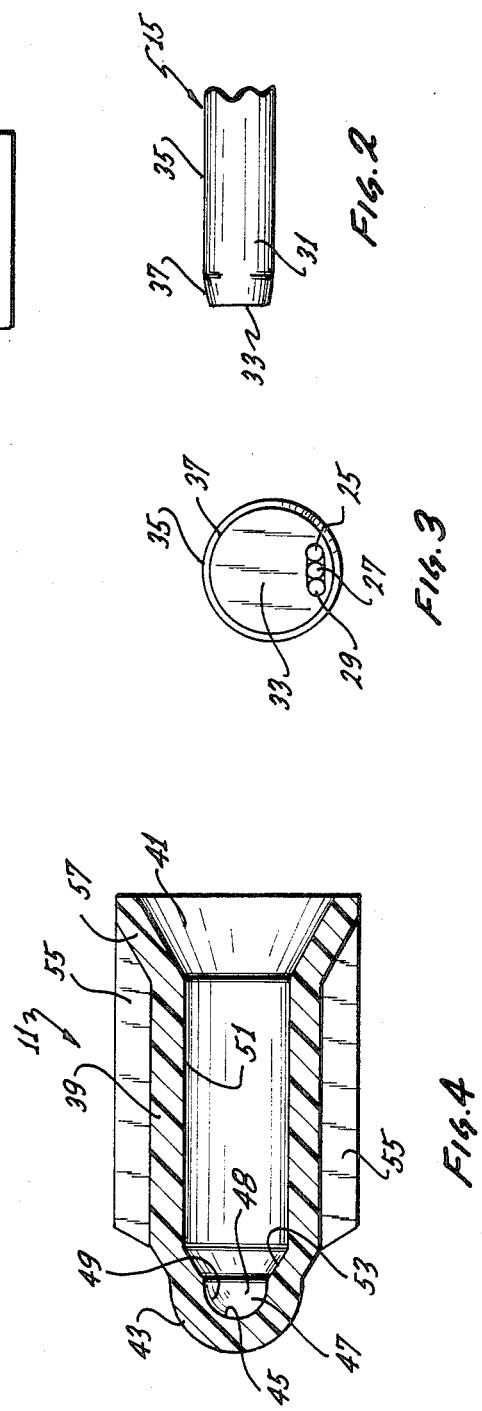

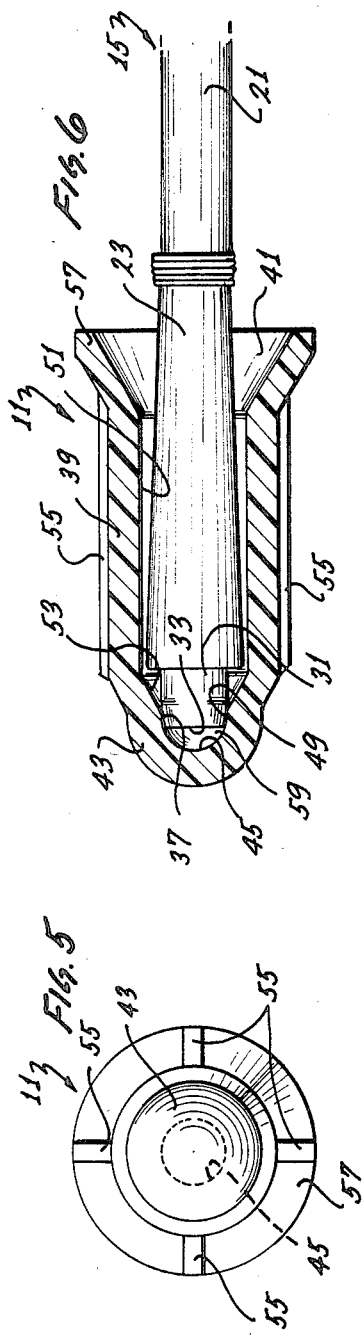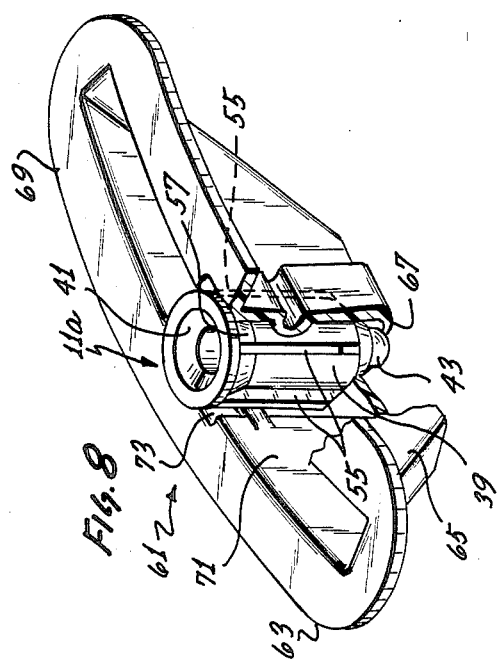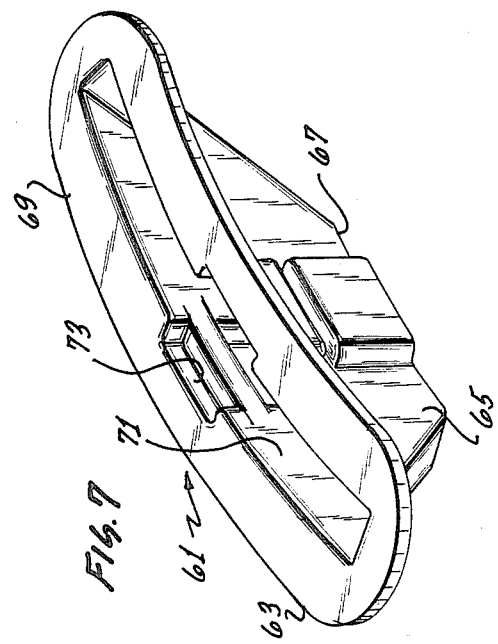

METHOD AND APPARATUS FOR IN VITRO CALIBRATION OF OXYGEN SATURATION MONITOR

BACKGROUND OF THE INVENTION

A variety of optical measuring systems must be calibrated prior to use. One example of such a system is an oximetry system which must provide accurate in vivo measurements of mixed venous oxygen saturation. A system of this type includes an optical thermodilution catheter, a light source for supplying light at selected wavelengths to the optical catheter, and an optical measuring device for measuring the intensity of the light signal received from the optical catheter. Any of these components can introduce variations into the system, and thus, the entire system must be calibrated.

The oximetry system can be calibrated using in vivo techniques. According to this approach, an oximeter catheter is inserted into the vascular system of a patient, and light intensity measurements of the blood are made. A blood sample is also drawn from the patient, and the degree of oxygen saturation of the sample is accurately measured in a laboratory. These two measurements are then appropriately correlated to calibrate the oximetry system. This technique requires that a blood sample be drawn, and this can introduce error due to sampling techniques and due to time lags, such as the time lag between the sample time and the completion of the laboratory analysis of the sample. In addition, this technique is very time consuming.

The optical system can also be calibrated using in vitro techniques. One such technique requires that a reference element be brought into optical contact with the end of an optical catheter while the catheter is clamped in position. The clamping of the optical catheter, particularly in the region of the balloon, may damage the balloon. In addition, a mechanism for moving the reference element is required. This technique also requires that the reference element be compliant at the surface which contacts the end of the catheter. Such a device is shown in Shaw et al U.S. Pat. No. 4,322,164.

It is also known to employ an optically open system as shown in Polyani et al U.S. Pat. No. 4,050,450. However, being optically open, this system is not immune to ambient light.

SUMMARY OF THE INVENTION

This invention overcomes these disadvantages by providing a calibration reference apparatus which is immune to ambient light and which does not require that the end face of the optical catheter or other light guide be in contact with the operative surface of a calibration element. As a consequence, the mechanism of the prior art for moving the calibration element into contact with the end face of the light guide is eliminated. Also, the mechanical clamping device for clamping of the light guide is not required, and the calibration element need not be constructed of compliant material.

With this invention, the calibration element has a surface defining a cavity having an opening at one end, with the opening being sized to receive the end portion of the light guide. To provide immunity to ambient light and to prevent the escape of light from the cavity, the cavity is preferably, essentially optically closed, except for such opening. If desired, the cavity may have other openings, provided such openings do not permit the transmission of significant light through such openings.

Means is provided for releasably positioning the end portion of the light guide in the cavity, with the end face of the light guide spaced from the surface of the cavity opposite the opening to define a gap. Accordingly, the light guide can direct light at least at one wavelength from the end face thereof across the gap and against the surface of the cavity.

The calibration element and the gap are adapted to return a known ratio of the light at such one wavelength which is directed into the gap from the end face of the light guide. Accordingly, contact between the calibration element and the end face of the light guide are not required. The light returned is returned to the light guide for transmission proximally along the light guide to a measuring device which measures the intensity of the light returned. This information is utilized in calibration of the light guide and the other components of the system.

The surface which defines the cavity need not be compliant and is preferably rigid. This surface is preferably symmetrical in a direction which will permit the end portion of the light guide to be inserted into the cavity in any angular orientation without affecting the ratio of the light which is returned. A preferred configuration is part spherical.

The optical properties of the calibration element must be known and be repeatable from element to element in production. This is necessary so that the calibration element will do its part to return the known ratio of light at the wavelength or wavelengths of interest back to the end face of the light guide. The optical properties of the calibration element should be homogeneous so that the ratio of light returned is not affected by the relative angular orientation of the calibration element and the end portion of the light guide.

Preferably, certain optical characteristics of the calibration element mimic the substance with which the light guide is adapted for use. For example, in the case of an oximetry system, the calibration element preferably has light returning properties which mimic blood. More specifically, the calibration element preferably has light-scattering, absorption and reflection properties which, in the aggregate (but not necessarily individually), mimic blood. In order to provide the calibration element with the desired light-scattering properties, the calibration element preferably includes a plurality of light-scattering particles distributed in a matrix.

It is preferred that essentially none of the light directed into the gap from the end face of the light guide be allowed to escape from the calibration reference apparatus, except back through the light guide. This can be accomplished, for example, by constructing the calibration element sufficiently thick and/or opaque to the wavelengths of interest so that essentially none of this light is transmitted completely through the calibration element. Alternatively, the calibration element may be at least partially received in an essentially opaque optical barrier element. In either case, the surface of the cavity surrounds the gap to at least assist in essentially preventing transmission of light at the wavelength of interest directed into the gap from the end face of the light guide radially of the gap to outside of the calibration reference device.

One important function of the positioning means for the light guide is that the positioning means establishes the size of the gap, and the size of the gap should be repeatable so that the light-attenuating effects of the gap will be repeatable. Although it is not necessary that the gap size be completely identical from unit to unit, the gap size should be repeatable within some reasonable tolerances. To meet these requirements in a simple, inexpensive construction, the position means can advantageously include a portion of the surface which defines the cavity, with such surface portion being adapted to form a friction fit with the end portion of the light guide. To assist in providing repeatability, this surface is preferably rigid so that it will allow the light guide to enter the cavity a predetermined amount.

The calibration reference apparatus can be of simple and inexpensive construction and be disposable. For example, the calibration reference apparatus may take the form of a calibration cup which comprises an elongated peripheral tubular wall open at one end and an end wall closing the other end of the tubular wall. The tubular wall and the end wall can be integrally molded. With this construction, the end wall defines the cavity, and the cavity is curved and opens toward the open end of the tubular wall. The calibration cup is adapted to receive the light guide through the tubular wall and in the cavity. Thus, the end wall provides the calibration reference element for use in calibrating the light guide and the associated components.

The invention, together with additional features and advantages thereof, may best be understood by reference to the following description, taken in connection with the accompanying illustrative drawing.

BRIEF DESCRIPTION OF THE DRAWING

FIG. 1 is a somewhat schematic illustration of one form of calibration reference apparatus constructed in accordance with the teachings of this invention and an optical oximeter catheter system.

FIG. 2 is a fragmentary side elevational view of a distal end portion of the optical catheter.

FIG. 3 is an end elevational view of the catheter.

FIG. 4 is a sectional view taken on an axial plane through the calibration reference apparatus.

FIG. 5 is an end elevational view of the calibration reference apparatus.

FIG. 6 is a sectional view similar to FIG. 4, with the end portion of the optical catheter being positioned in the calibration reference apparatus.

FIG. 7 is an isometric view of an optical barrier.

FIG. 8 is an isometric view of the calibration element with portions broken away and of the optical barrier element.

DESCRIPTION OF THE PREFERRED EMBODIMENTS

FIG. 1 shows a rigid calibration reference apparatus 11 being used with an oximeter catheter system 13. The oximeter catheter system 13 is conventional and may comprise, for example, an optical oximeter catheter 15, a light source 17 and a measuring and processing apparatus 19. The oximeter catheter 15 comprises a catheter body 21 and a balloon 23 and constitutes a light guide in that it includes a sending light conductor 25 (FIG. 3) and a receiving light conductor 27 retained within a passage of the catheter body by an elongated element 29. The catheter 15 has a distal end portion 31 and terminates in a distal end face 33. Although various constructions are possible, in this embodiment, the catheter body 21 is cylindrical and has a cylindrical peripheral surface 35 which is joined to the end face 33 by a curved surface 37 so that the diameter of the end face 33 is slightly less than the diameter of the peripheral surface 35. For example, the diameters of the peripheral surface 35 and the end face 33 may be 0.105 inch and 0.093 inch, respectively. In this embodiment, the end face 33 is planar and is perpendicular to the axis of the peripheral surface 35.

In use, the catheter 15 is inserted into the pulmonary artery using known techniques, and light from the light source 17 is transmitted along the sending light conductor 25, which may be an optical fiber, to the end face 33 where it impinges upon the blood in the vein. The blood scatters, reflects and absorbs some of the light from the light conductor 25 and returns a portion of the light along the receiving light conductor 27 to the measuring and processing apparatus 19. By comparing the intensities of light returned by the blood at two or more wavelengths to the apparatus 19, the oxygen saturation of the venous blood can be determined in accordance with known techniques. For this purpose, the light source 17 may transmit light at a selected wavelength or wavelengths depending upon the algorithm being employed.

If the system 13 were used without calibration, the catheter 15, the light source 17 and/or the apparatus 19 may introduce variables into the system which would prevent an accurate determination of oxygen saturation. Accordingly, prior to use of the apparatus 13, it is calibrated using the calibration reference apparatus 11.

As shown in FIG. 4, the calibration reference apparatus 11 is in the form of an integrally molded calibration cup which comprises an elongated, peripheral, tubular wall 39 having an opening 41 at its proximal end and a curved, rigid end wall 43 closing the other end of the tubular wall. The end wall 43 constitutes a calibration element, and it has a rigid, imperforate hemispherical surface 45 defining a hemispherical cavity 47 coaxial with the tubular wall 39. The cavity 47 has an opening 48 at the proximal end of the cavity which faces toward the opening 41. Except for the opening 48, the cavity 47 is closed. The surface 45 blends smoothly into a very short surface extension 49 which is joined to an elongated, inner cylindrical surface 51 by a conical guide surface 53. The tubular wall 39 is stiffened by four axially extending, external wings or ribs 55, and a proximal region of the tubular wall 39 is flared radially outwardly in a conical lead-in section 57 for protection of the balloon 23.

In the embodiment illustrated, the calibration reference apparatus 11 comprises a plurality of light-scattering particles distributed in a matrix of plastic material, and the plastic material includes a dye. Although many rigid, non-toxic, and sterilizable materials may be utilized, polyethylene 306 is currently preferred for the matrix.

The light-scattering particles may be, for example, oxides, carbonates and sulfates. However, titanium dioxide, particles are preferred for use with polyethylene. Although particle size can vary, in the preferred range of particle sizes, at least 99 percent of the particles will pass a 325 mesh screen.

Various non-toxic dyes may be used. The dye is used primarily for light absorption and as a secondary light scatterer. In the illustrated embodiment, FDC Red Lake No. 3 dye is utilized.

These ingredients may be mixed in various proportions depending upon the results desired. Thus, to increase light scattering, a greater percentage of light-scattering particles should be used. Similarly, to increase light absorption, the percent of dye should be increased. In the illustrated embodiment, the apparatus 11 consists of 0.17 percent by weight of titanium dioxide, 0.5 percent by weight FDC Red Lake No. 3 dye with the remainder being polyethylene 306. The ingredients of the apparatus 11 are mixed homogeneously so that the surface 45 and the end wall 43 will have homogeneous optical properties and be repeatable in production so that when a large number of the calibration apparatuses 11 are molded, each of the end walls and associated surfaces 45 will have substantially the same reflection, absorption, and scattering properties. The preferred ingredients and proportions stated above provide light-scattering, absorption and reflection properties which, in the aggregate, mimic blood.

The surface finish of the surface 45 is carefully controlled so that it will be the same in production from calibration element to calibration element. The surface 45 may have various degrees of smoothness and may be, for example, smooth, rough or matted. In this embodiment, the surface 45 is very smooth and has a 20-micron surface finish.

In use of the apparatus 11, the end portion 31 of the catheter 15 is inserted through the opening 41 and is guided by the tubular wall 39 and the conical surface 53 into the cavity 47. The diameter of the cavity 47 is slightly smaller than the diameter of the peripheral surface 35. Because the cavity 47 is of progressively reducing cross-sectional area as it extends distally, the end portion 31 of the catheter 15 can be forced into the cavity 47 for only a short distance as shown in FIG. 6. Specifically, the outer or proximal regions or portions of the surface 45 form a friction fit with the very distal tip of the end portion 31. Thus, this portion of the surface 45 constitutes means for releasably positioning the end portion 31 of the catheter 15 in the cavity 47. In this position, the end face 33 is spaced from a region of the surface 45 to form a gap 59. This outer portion of the surface 45 can also be considered as a stop for arresting further inward movement of the end portion 31 into the cavity 47. By sizing of the surface 45 and the cavity 47 with respect to the end portion 31, the axial dimension of the gap 59 can be predicted with sufficient accuracy to provide adequate calibration of the system 13.

With the components in the position of FIG. 6, light from the light source 17 is directed through the sending light conductor 25 to the end face 33. The light can then be directed at the wavelength of interest from the end face thereof across the gap 59 and against the surface 45. ratio of the light which is directed into the gap from the end face 33. The intensity of the light returned at two or more wavelengths is measured by the apparatus 19 and compared with the known ideal rates. Adjustments are then made in the apparatus 19 to obtain calibration of the apparatus 11.

In the form shown in FIG. 4, the calibration reference apparatus is assumed to be of sufficient thickness so that essentially none of the light directed into the gap 50 from the end face 33 of the catheter 15 is transmitted completely through the end wall 43. This same effect can be obtained by utilizing an end wall 43 which would transmit more light than is desirable out of the gap 53. When using an end wall 43 of this latter type, it is preferred to use an opaque optical barrier element, such as the barrier element 61, FIG. 7. Although the barrier element 61 can be of various different constructions, in the form illustrated, it is integrally molded of plastic material and includes a relatively wide receptacle 63 which includes a peripheral wall 65 with tapered ends, an end wall 67, and a flange 69 around an opening 71. The opening 71 is widened at a central region 73, and the receptacle 63 may be curved to facilitate loading it in a curved groove of a catheter package (not shown). The peripheral wall 65 and the end wall 67 are opaque, and preferably the interior and exterior surfaces of these surfaces are white to maximize reflection.

The optical barrier element 61 can be used with a calibration reference apparatus 11a as shown in FIG. 8. The calibration reference apparatus 11a is identical to the calibration reference apparatus 11, except that it would transmit a greater percentage of light through the end wall 43 at the wavelengths of interest.

In use, the apparatus 11a is inserted into the opening 71 at the central region 73 to place the end wall 43 in contact with the end wall 67. The interior surface of the end wall 67 may have a rounded, shallow cavity for receiving, or partly receiving, the end wall 43. Thus, an optical barrier around the end wall 43 is provided by the optical barrier 61. By making the opening 71 relatively long, additional widened regions, such as the region 73 can be provided, if desired, so that a single optical barrier element 61 can be used for two or more of the calibration reference apparatuses.

Although exemplary embodiments of the invention have been shown and described, many changes, modifications and substitutions may be made by one having ordinary skill in the art without necessarily departing from the spirit and scope of this invention.

I claim:

1. A calibration reference apparatus for use with a light guide having an end portion which terminates in an end face, said apparatus comprising:
   a calibration element having a surface defining a cavity, said cavity having an opening at one end and otherwise being essentially optically closed, said opening being sized to receive the end portion of a light guide;
   means for releasably positioning the end portion of a light guide in the cavity with the end face of the light guide spaced from said surface opposite said opening to define a gap whereby a light guide can direct light at least at one wavelength from the end face thereof across the gap and against said surface opposite said opening;
   said calibration element having means for returning some of the light at said one wavelength which is directed against said surface opposite said opening; said means for returning having similar light returning properties as blood; and
   said positioning means and said calibration element being fixed with respect to each other.

2. An apparatus as defined in claim 1 wherein said surface is part spherical.

3. An apparatus as defined in claim 1 wherein said positioning means includes a portion of said surface, said portion of said surface being rigid and adapted to form a friction fit with the end portion of a light guide.

4. An apparatus as defined in claim 1 wherein the calibration element is constructed of a material that essentially allows no light of said one wavelength directed against said surface opposite said opening to be transmitted completely through the calibration element.

5. An apparatus as defined in claim 1 including an essentially opaque optical barrier element at least partially receiving the calibration element.

6. An apparatus as defined in claim 1 wherein said means for returning includes a matrix and a plurality of light scattering particles distributed in said matrix.

7. An apparatus as defined in claim 1 including an elongated tubular wall integral with the calibration element for guiding a light guide into said cavity.

8. A calibration reference apparatus as defined in claim 1 wherein said surface has homogeneous optical properties.

9. A calibration reference apparatus for use with a light guide having an end portion which terminates in an end face, said apparatus comprising:
a matrix;
a plurality of light scattering particles dispersed in said matrix;
means for holding the end portion of a light guide in predetermined spaced relationship with a region of the matrix to define a gap between the end face of the light guide and said region of the matrix whereby the light guide can direct light at least at one wavelength into the gap and toward the matrix;
said matrix being adapted to return some of the light at said one wavelength directed into the gap from the end face of the light guide;
means surrounding the gap to essentially prevent transmission of the light at said one wavelength directed into the gap from the end face of the light guide radially of the gap to the outside of the calibration reference device; and
said matrix and said surrounding means being fixed with respect to each other.

10. An apparatus as defined in claim 9 wherein said matrix is constructed of plastic and includes dye.

11. A calibration cup comprising:
an elongated peripheral tubular wall open at one end and an end wall closing the other end of the tubular wall, said tubular wall and said end wall being integrally molded;
said end wall defining a curved cavity opening toward the open end of the tubular wall, said calibration cup being adapted to receive a light guide through the tubular wall and in the cavity;
said end wall having light-scattering, absorption and reflection properties which in the aggregate are similar to blood;
said end wall including a matrix of plastic material and a plurality of light scattering particles distributed in said matrix and said cavity is part spherical; and
a stop means for limiting the extent to which a light guide can be advanced into said cavity whereby an end face of the light guide can be spaced from a region of the end wall to define a gap and said end wall is adapted to return a ratio of the light directed into the cavity from the end face of the light guide.

12. A calibration cup as defined in claim 11 including an essentially opaque barrier element at least partially receiving the calibration element.

13. An assembly comprising:
an elongated peripheral tubular wall open at one end and an end wall closing the other end of the tubular wall, said tubular wall and said end wall being integrally molded;
an optical catheter having an end portion which terminates in an end face and light-conducting means for conducting light along the length of the catheter to and from said end face;
said end wall defining a curved cavity opening toward the open end of the tubular wall, said tubular wall receiving the end portion of the optical catheter; and
a stop for limiting the extent to which the end portion can be advanced into the cavity whereby the end face of the optical catheter is spaced from a region of the end wall to define a gap and said end wall and the gap being adapted to return some of the light directed into the cavity from the end face.

14. An assembly comprising:
a calibration reference apparatus including a calibration element having a curved surface defining a cavity, said cavity having an opening at one end and otherwise being optically closed, at least a portion of said curved surface being generally opposite said opening;
an optical catheter having an end portion which terminates in an end face and light-conducting means for conducting light along the length of the catheter to and from said end face;
said opening of said cavity being sized to receive the end portion of the optical catheter;
means for positioning the end portion of the optical catheter in the cavity with the end face of the optical catheter being spaced from said surface opposite said opening to define a gap whereby the optical catheter can direct light at least at one wavelength from the end face thereof into the gap;
said calibration element being adapted to return some of the light at said one wavelength directed into the gap from the end face of the optical catheter; and
said positioning means including means for preventing the optical catheter from being advanced into the cavity far enough to eliminate said gap between said end face and said surface.

15. A method of calibrating a light guide having an end portion which terminates in an end face and light-conducting means for conducting light along the length of the catheter to and from the end face, said method comprising:
providing a calibration element having a surface defining a cavity, said cavity having an opening at one end and otherwise being closed, and said opening being sized to receive the end portion of the light guide;
inserting the end portion of the light guide into the cavity to a position in which the end face of the light guide is spaced from said surface opposite said opening to define a gap;
directing light at least at one wavelength through the light-conducting means and said gap and against said surface;
allowing the calibration element and the air gap to return a known ratio of the light at said one wavelength directed into the gap from the light-conducting means back through the light-conducting means;
measuring the intensity of the light returned through the light-conducting means; and
utilizing the information obtained in said step of measuring in the calibration of the light guide.

* * * * *

UNITED STATES PATENT AND TRADEMARK OFFICE
CERTIFICATE OF CORRECTION

PATENT NO. : 4,796,633

DATED : January 10, 1989

INVENTOR(S) : Lori J. Zwirkoski

It is certified that error appears in the above-identified patent and that said Letters Patent is hereby corrected as shown below:

On the Title Page, Item [57], in the Abstract, line 9, change "extend" to -- extent --.

Column 8, line 58 change "a known ratio " to -- some --.

Signed and Sealed this

Eleventh Day of July, 1989

Attest:

DONALD J. QUIGG

Attesting Officer

Commissioner of Patents and Trademarks